United States Patent
Itoh et al.

(10) Patent No.: US 7,238,777 B2
(45) Date of Patent: Jul. 3, 2007

(54) AGENTS FOR ADSORPTION AND BRIDGING FOR ADENOVIRUS

(75) Inventors: Akira Itoh, Shizuoka (JP); Yutaka Hanazono, Tochigi (JP); Takashi Okada, Tochigi (JP); Keiya Ozawa, Tochigi (JP)

(73) Assignee: Asahi Kasei Kabushiki Kaisha, Osaka-shi (JP)

( * ) Notice: Subject to any disclaimer, the term of this patent is extended or adjusted under 35 U.S.C. 154(b) by 625 days.

(21) Appl. No.: 10/270,555

(22) Filed: Oct. 16, 2002

(65) Prior Publication Data

US 2003/0092068 A1 May 15, 2003

(30) Foreign Application Priority Data

Oct. 16, 2001 (JP) ............................. 2001-317766

(51) Int. Cl.
*C07K 1/00* (2006.01)

(52) U.S. Cl. ...................... 530/350; 530/300
(58) Field of Classification Search ............. 435/69.1; 530/350, 388.22, 388.7, 402, 300; 424/130.1
See application file for complete search history.

(56) References Cited

U.S. PATENT DOCUMENTS

| | | | |
|---|---|---|---|
| 5,844,089 A * | 12/1998 | Hoffman et al. ............ 530/385 |
| 6,287,857 B1 | 9/2001 | O'Riordan et al. |
| 6,524,572 B1 * | 2/2003 | Li ............................. 424/93.2 |
| 6,555,367 B1 * | 4/2003 | Spence et al. ........... 435/320.1 |

FOREIGN PATENT DOCUMENTS

| | | | |
|---|---|---|---|
| EP | 1 083 226 A1 | | 3/2001 |
| JP | 10-155489 A | | 6/1998 |
| WO | WO 99/19500 | * | 4/1999 |
| WO | WO 99/40214 A2 | | 8/1999 |

OTHER PUBLICATIONS

Sehgal et al. Retroviral transduction of quiescent haematopoietic cells using a packaging cell line expressing the membrane bound form of stem cell factor. Gene Therapy 1999 vol. 6, pp. 1084-1091.*
B. Breyer et al., *Current Gene Therapy*, vol. 1, pp. 149-162, 2001.
F. C. Marini III et al., *Cancer Gene Therapy*, vol. 7, No. 6, pp. 816-825, 2000.
J. M. Bergelson et al., *Science*, vol. 275, pp. 1320-1323, Feb. 28, 1997.
T. J. Wickham et al., *Cell*, vol. 73, pp. 309-319, Apr. 23, 1993.
V. I. Rebel et al., *Stem Cells*, vol. 18, pp. 176-182, 2000.
R. P. Leon et al., *Proc. Natl. Acad. Sci. USA*, vol. 95, pp. 13159-13164, Oct. 1998.
J. S. Smith et al., *Proc. Natl. Acad. Sci. USA*, vol. 96, pp. 8855-8860, Aug. 1999.
D. M. Shayakhmetov et al., *Journal of Virology*, vol. 74, No. 6, pp. 2567-2583, Mar. 2000.
T. Watanabe et al., *Blood*, vol. 87, No. 12, pp. 5032-5039, Jun. 15, 1996.
S. J. Neering et al., *Blood*, vol. 88, No. 4, pp. 1147-1155, Aug. 15, 1996.
T. Takahashi et al., *Blood*, vol. 91, No. 12, pp. 4509-4515, Jun. 15, 1998.
X. Fan et al., *Human Gene Therapy*, vol. 11, pp. 1313-1327, Jun. 10, 2000.
K. L. MacKenzie et al., *Blood*, vol. 96, No. 1, pp. 100-108, Jul. 1, 2000.
I. Dmitriev et al., *Journal of Virology*, vol. 74, No. 15, pp. 6875-6884, Aug. 2000.
C. Ebbinghaus et al., *Journal of Virology*, vol. 75, No. 1, pp. 480-489, Jan. 2001.
P. Freimuth et al., *Journal of Virology*, vol. 73, No. 2, pp. 1392-1398, Feb. 1999.
Z. Zuo et al., *Protein Engineering*, vol. 13, No. 5, pp. 361-367, 2000.

* cited by examiner

*Primary Examiner*—Bruce R. Campell
*Assistant Examiner*—Myron G. Hill
(74) *Attorney, Agent, or Firm*—Birch, Stewart, Kolasch & Birch, LLP

(57) ABSTRACT

The object of the present invention is to provide an agent for specific adsorption of type 5 adenoviral vector to undifferentiated blood cells which enables infection with a viral concentration that does not impart toxicity to undifferentiated blood cells, without requiring the construction of a new viral genome, or special modification of viral particles such as biotination, etc. The above objective has been achieved by providing a polypeptide which has affinity for both adenovirus and undifferentiated blood cells. Use of the polypeptide of the present invention enables improved efficiency of adenoviral vector-mediated gene transfer of any gene to undifferentiated blood cells, and there is provided a method of introducing any gene for which transient expression in these cells is desired. In particular, the method is useful for intracellular DNA recombination by transiently expressing site-specific recombinase, and for induction into any cells of different lines by transient expression of master genes.

4 Claims, 2 Drawing Sheets

1.

N-terminus  C-terminus

2.

N-terminus  C-terminus

3.

CAR extracellular region affinity region for undifferentiated blood cells

Fc region

```
                            SEQUENCE LISTING

<160> NUMBER OF SEQ ID NOS: 13

<210> SEQ ID NO 1
<211> LENGTH: 393
<212> TYPE: PRT
<213> ORGANISM: Artificial Sequence
<220> FEATURE:
<223> OTHER INFORMATION: a fusion protein of human CAR and human SCF
      with an artificial linker sequence

<400> SEQUENCE: 1

Leu Ser Ile Thr Thr Pro Glu Glu Met Ile Glu Lys Ala Lys Gly Glu
 1               5                  10                  15

Thr Ala Tyr Leu Pro Cys Lys Phe Thr Leu Ser Pro Glu Asp Gln Gly
             20                  25                  30

Pro Leu Asp Ile Glu Trp Leu Ile Ser Pro Ala Asp Asn Gln Lys Val
         35                  40                  45

Asp Gln Val Ile Ile Leu Tyr Ser Gly Asp Lys Ile Tyr Asp Asp Tyr
     50                  55                  60

Tyr Pro Asp Leu Lys Gly Arg Val His Phe Thr Ser Asn Asp Leu Lys
 65                  70                  75                  80

Ser Gly Asp Ala Ser Ile Asn Val Thr Asn Leu Gln Leu Ser Asp Ile
                 85                  90                  95

Gly Thr Tyr Gln Cys Lys Val Lys Lys Ala Pro Gly Val Ala Asn Lys
            100                 105                 110

Lys Ile His Leu Val Val Leu Val Lys Pro Ser Gly Ala Arg Cys Tyr
        115                 120                 125

Val Asp Gly Ser Glu Glu Ile Gly Ser Asp Phe Lys Ile Lys Cys Glu
    130                 135                 140

Pro Lys Glu Gly Ser Leu Pro Leu Gln Tyr Glu Trp Gln Lys Leu Ser
145                 150                 155                 160

Asp Ser Gln Lys Met Pro Thr Ser Trp Leu Ala Glu Met Thr Ser Ser
                165                 170                 175

Val Ile Ser Val Lys Asn Ala Ser Ser Glu Tyr Ser Gly Thr Tyr Ser
            180                 185                 190

Cys Thr Val Arg Asn Arg Val Gly Ser Asp Gln Cys Leu Leu Arg Leu
        195                 200                 205

Asn Val Val Pro Pro Ser Asn Lys Ala His His His His His His Ser
    210                 215                 220

Ala Ser Ala Ser Ala Glu Gly Ile Cys Arg Asn Arg Val Thr Asn Asn
225                 230                 235                 240

Val Lys Asp Val Thr Lys Leu Val Ala Asn Leu Pro Lys Asp Tyr Met
                245                 250                 255

Ile Thr Leu Lys Tyr Val Pro Gly Met Asp Val Leu Pro Ser His Cys
            260                 265                 270
```

```
Trp Ile Ser Glu Met Val Val Gln Leu Ser Asp Ser Leu Thr Asp Leu
        275                 280                 285

Leu Asp Lys Phe Ser Asn Ile Ser Glu Gly Leu Ser Asn Tyr Ser Ile
        290                 295                 300

Ile Asp Lys Leu Val Asn Ile Val Asp Asp Leu Val Glu Cys Val Lys
305                 310                 315                 320

Glu Asn Ser Ser Lys Asp Leu Lys Lys Ser Phe Lys Ser Pro Glu Pro
                325                 330                 335

Arg Leu Phe Thr Pro Glu Glu Phe Phe Arg Ile Phe Asn Arg Ser Ile
        340                 345                 350

Asp Ala Phe Lys Asp Phe Val Val Ala Ser Glu Thr Ser Asp Cys Val
        355                 360                 365

Val Ser Ser Thr Leu Ser Pro Glu Lys Asp Ser Arg Val Ser Val Thr
        370                 375                 380

Lys Pro Phe Met Leu Pro Pro Val Ala
385                 390

<210> SEQ ID NO 2
<211> LENGTH: 393
<212> TYPE: PRT
<213> ORGANISM: Artificial Sequence
<220> FEATURE:
<223> OTHER INFORMATION: a fusion protein of human CAR and mouse SCF
      with an artificial linker sequence

<400> SEQUENCE: 2

Leu Ser Ile Thr Thr Pro Glu Glu Met Ile Glu Lys Ala Lys Gly Glu
  1               5                  10                  15

Thr Ala Tyr Leu Pro Cys Lys Phe Thr Leu Ser Pro Glu Asp Gln Gly
             20                  25                  30

Pro Leu Asp Ile Glu Trp Leu Ile Ser Pro Ala Asp Asn Gln Lys Val
         35                  40                  45

Asp Gln Val Ile Ile Leu Tyr Ser Gly Asp Lys Ile Tyr Asp Asp Tyr
     50                  55                  60

Tyr Pro Asp Leu Lys Gly Arg Val His Phe Thr Ser Asn Asp Leu Lys
 65                  70                  75                  80

Ser Gly Asp Ala Ser Ile Asn Val Thr Asn Leu Gln Leu Ser Asp Ile
                 85                  90                  95

Gly Thr Tyr Gln Cys Lys Val Lys Ala Pro Gly Val Ala Asn Lys
             100                 105                 110

Lys Ile His Leu Val Val Leu Val Lys Pro Ser Gly Ala Arg Cys Tyr
        115                 120                 125

Val Asp Gly Ser Glu Glu Ile Gly Ser Asp Phe Lys Ile Lys Cys Glu
        130                 135                 140

Pro Lys Glu Gly Ser Leu Pro Leu Gln Tyr Glu Trp Gln Lys Leu Ser
145                 150                 155                 160

Asp Ser Gln Lys Met Pro Thr Ser Trp Leu Ala Glu Met Thr Ser Ser
                165                 170                 175

Val Ile Ser Val Lys Asn Ala Ser Ser Glu Tyr Ser Gly Thr Tyr Ser
            180                 185                 190

Cys Thr Val Arg Asn Arg Val Gly Ser Asp Gln Cys Leu Leu Arg Leu
        195                 200                 205

Asn Val Val Pro Pro Ser Asn Lys Ala His His His His His His Ser
        210                 215                 220

Ala Ser Ala Ser Ala Lys Glu Ile Cys Gly Asn Pro Val Thr Asp Asn
```

-continued

```
                225                 230                 235                 240
Val Lys Asp Ile Thr Lys Leu Val Ala Asn Leu Pro Asn Asp Tyr Met
                    245                 250                 255

Ile Thr Leu Asn Tyr Val Ala Gly Met Asp Val Leu Pro Ser His Cys
                    260                 265                 270

Trp Leu Arg Asp Met Val Ile Gln Leu Ser Leu Ser Leu Thr Thr Leu
                    275                 280                 285

Leu Asp Lys Phe Ser Asn Ile Ser Glu Gly Leu Ser Asn Tyr Ser Ile
                    290                 295                 300

Ile Asp Lys Leu Gly Lys Ile Val Asp Asp Leu Val Leu Cys Met Glu
305                 310                 315                 320

Glu Asn Ala Pro Lys Asn Ile Lys Ser Pro Lys Arg Pro Glu Thr
                    325                 330                 335

Arg Ser Phe Thr Pro Glu Glu Phe Ser Ile Phe Asn Arg Ser Ile
                    340                 345                 350

Asp Ala Phe Lys Asp Phe Met Val Ala Ser Asp Thr Ser Asp Cys Val
                    355                 360                 365

Leu Ser Ser Thr Leu Gly Pro Glu Lys Asp Ser Arg Val Ser Val Thr
                    370                 375                 380

Lys Pro Phe Met Leu Pro Pro Val Ala
385                 390
```

<210> SEQ ID NO 3
<211> LENGTH: 474
<212> TYPE: PRT
<213> ORGANISM: Artificial Sequence
<220> FEATURE:
<223> OTHER INFORMATION: a fusion protein of human CAR and a single
      chain Fv derived from mouse monoclonal antibody against human CD34
      with an artificial linker sequence

<400> SEQUENCE: 3

```
Leu Ser Ile Thr Thr Pro Glu Glu Met Ile Glu Lys Ala Lys Gly Glu
1               5                   10                  15

Thr Ala Tyr Leu Pro Cys Lys Phe Thr Leu Ser Pro Glu Asp Gln Gly
                20                  25                  30

Pro Leu Asp Ile Glu Trp Leu Ile Ser Pro Ala Asp Asn Gln Lys Val
            35                  40                  45

Asp Gln Val Ile Ile Leu Tyr Ser Gly Asp Lys Ile Tyr Asp Asp Tyr
        50                  55                  60

Tyr Pro Asp Leu Lys Gly Arg Val His Phe Thr Ser Asn Asp Leu Lys
65                  70                  75                  80

Ser Gly Asp Ala Ser Ile Asn Val Thr Asn Leu Gln Leu Ser Asp Ile
                85                  90                  95

Gly Thr Tyr Gln Cys Lys Val Lys Lys Ala Pro Gly Val Ala Asn Lys
                100                 105                 110

Lys Ile His Leu Val Val Leu Val Lys Pro Ser Gly Ala Arg Cys Tyr
            115                 120                 125

Val Asp Gly Ser Glu Glu Ile Gly Ser Asp Phe Lys Ile Lys Cys Glu
        130                 135                 140

Pro Lys Glu Gly Ser Leu Pro Leu Gln Tyr Glu Trp Gln Lys Leu Ser
145                 150                 155                 160

Asp Ser Gln Lys Met Pro Thr Ser Trp Leu Ala Glu Met Thr Ser Ser
                165                 170                 175

Val Ile Ser Val Lys Asn Ala Ser Ser Glu Tyr Ser Gly Thr Tyr Ser
                180                 185                 190
```

-continued

```
Cys Thr Val Arg Asn Arg Val Gly Ser Asp Gln Cys Leu Leu Arg Leu
        195                 200                 205
Asn Val Val Pro Pro Ser Asn Lys Ala His His His His His Ser
    210                 215                 220
Ala Ser Ala Ser Ala Gln Val Gln Leu Lys Gln Ser Gly Pro Gly Leu
225                 230                 235                 240
Val Gln Pro Ser Gln Ser Leu Ser Phe Ile Cys Thr Val Ser Gly Phe
                245                 250                 255
Ser Leu Thr Ser His Gly Val His Trp Val Arg Gln Ser Pro Gly Lys
            260                 265                 270
Gly Leu Glu Trp Leu Gly Val Ile Trp Gly Ala Gly Arg Thr Asp Tyr
        275                 280                 285
Asn Ala Ala Phe Ile Ser Arg Leu Ser Ile Ser Arg Asp Ile Ser Lys
    290                 295                 300
Ser Gln Val Phe Phe Lys Met Asn Ser Leu Gln Val Asp Asp Thr Ala
305                 310                 315                 320
Ile Tyr Tyr Cys Ala Arg Asn Arg Tyr Glu Ser Tyr Phe Asp Tyr Trp
                325                 330                 335
Gly Gln Gly Thr Thr Val Thr Val Ser Ser Gly Gly Gly Ser Gly
            340                 345                 350
Gly Gly Gly Ser Gly Gly Gly Ser Asp Ile Glu Leu Thr Gln Ser
        355                 360                 365
Pro Leu Ser Leu Pro Val Ser Leu Gly Asp Gln Ala Ser Ile Ser Cys
    370                 375                 380
Arg Ser Ser Gln Asn Leu Val His Ser Asn Gly Asn Thr Tyr Leu His
385                 390                 395                 400
Trp Tyr Leu Gln Lys Pro Gly Gln Ser Pro Asn Leu Leu Ile Tyr Lys
                405                 410                 415
Val Ser Asn Arg Phe Ser Gly Val Pro Asp Arg Phe Ser Gly Ser Gly
            420                 425                 430
Ser Gly Thr Glu Phe Thr Leu Lys Ile Ser Arg Val Glu Ala Glu Asp
        435                 440                 445
Leu Gly Val Tyr Phe Cys Ser Gln Ser Thr His Val Pro Leu Thr Phe
    450                 455                 460
Gly Ala Gly Thr Lys Val Glu Leu Lys Arg
465                 470
```

<210> SEQ ID NO 4
<211> LENGTH: 1256
<212> TYPE: DNA
<213> ORGANISM: Artificial Sequence
<220> FEATURE:
<223> OTHER INFORMATION: cDNA encoding a fusion protein of human CAR and
      human SCF with an artificial linker sequence

<400> SEQUENCE: 4

```
aagcttccac c atg gcg ctc ctg ctg tgc ttc gtg ctc ctg tgc gga gta        50
            Met Ala Leu Leu Leu Cys Phe Val Leu Leu Cys Gly Val
                         -15                 -10 gtg gat ttc gcc aga agt ttg agt atc act act cct gaa gag atg att         98
Val Asp Phe Ala Arg Ser Leu Ser Ile Thr Thr Pro Glu Glu Met Ile
    -5              -1   1                   5                  10 gaa aaa gcc aaa ggg gaa act gcc tat ctg cca tgc aaa ttt acg ctt       146
Glu Lys Ala Lys Gly Glu Thr Ala Tyr Leu Pro Cys Lys Phe Thr Leu
                15                  20                  25 agt ccc gaa gac cag gga ccg ctg gac atc gag tgg ctg ata tca cca       194
```

-continued

```
                Ser Pro Glu Asp Gln Gly Pro Leu Asp Ile Glu Trp Leu Ile Ser Pro
                            30                  35                  40 gct gat aat cag aag gtg gat caa gtg att att tta tat tct gga gac              242
Ala Asp Asn Gln Lys Val Asp Gln Val Ile Ile Leu Tyr Ser Gly Asp
            45                  50                  55 aaa att tat gat gac tac tat cca gat ctg aaa ggc cga gta cat ttt              290
Lys Ile Tyr Asp Asp Tyr Tyr Pro Asp Leu Lys Gly Arg Val His Phe
    60                  65                  70 acg agt aat gat ctc aaa tct ggt gat gca tca ata aat gta acg aat              338
Thr Ser Asn Asp Leu Lys Ser Gly Asp Ala Ser Ile Asn Val Thr Asn
75                  80                  85                  90 tta caa ctg tca gat att ggc aca tat cag tgc aaa gtg aaa aaa gct              386
Leu Gln Leu Ser Asp Ile Gly Thr Tyr Gln Cys Lys Val Lys Lys Ala
                95                  100                 105 cct ggt gtt gca aat aag aag att cac ctg gta gtt ctt gtt aag cct              434
Pro Gly Val Ala Asn Lys Lys Ile His Leu Val Val Leu Val Lys Pro
            110                 115                 120 tca ggt gcg aga tgt tac gtt gat gga tct gaa gaa att gga agt gac              482
Ser Gly Ala Arg Cys Tyr Val Asp Gly Ser Glu Glu Ile Gly Ser Asp
        125                 130                 135 ttt aag ata aaa tgt gaa cca aaa gaa ggt tca ctt cca tta cag tat              530
Phe Lys Ile Lys Cys Glu Pro Lys Glu Gly Ser Leu Pro Leu Gln Tyr
    140                 145                 150 gag tgg caa aaa ttg tct gac tca cag aaa atg ccc act tca tgg tta              578
Glu Trp Gln Lys Leu Ser Asp Ser Gln Lys Met Pro Thr Ser Trp Leu
155                 160                 165                 170 gca gaa atg act tca tct gtt ata tct gta aaa aat gcc tct tct gag              626
Ala Glu Met Thr Ser Ser Val Ile Ser Val Lys Asn Ala Ser Ser Glu
                175                 180                 185 tac tct ggg aca tac agc tgt aca gtc aga aac aga gtg ggc tct gat              674
Tyr Ser Gly Thr Tyr Ser Cys Thr Val Arg Asn Arg Val Gly Ser Asp
            190                 195                 200 cag tgc ctg ttg cgt cta aac gtt gtc cct cct tca aat aaa gct cat              722
Gln Cys Leu Leu Arg Leu Asn Val Val Pro Pro Ser Asn Lys Ala His
        205                 210                 215 cat cac cat cac cat agc gct tcc gcc tct gcc gaa ggg atc tgc agg              770
His His His His His Ser Ala Ser Ala Ser Ala Glu Gly Ile Cys Arg
    220                 225                 230 aat cgt gtg act aat aat gta aaa gac gtc act aaa ttg gtg gca aat              818
Asn Arg Val Thr Asn Asn Val Lys Asp Val Thr Lys Leu Val Ala Asn
235                 240                 245                 250 ctt cca aaa gac tac atg ata acc ctc aaa tat gtc ccc ggg atg gat              866
Leu Pro Lys Asp Tyr Met Ile Thr Leu Lys Tyr Val Pro Gly Met Asp
                255                 260                 265 gtt ttg cca agt cat tgt tgg ata agc gag atg gta gta caa ttg tca              914
Val Leu Pro Ser His Cys Trp Ile Ser Glu Met Val Val Gln Leu Ser
            270                 275                 280 gac agc ttg act gat ctt ctg gac aag ttt tca aat att tct gaa ggc              962
Asp Ser Leu Thr Asp Leu Leu Asp Lys Phe Ser Asn Ile Ser Glu Gly
        285                 290                 295 ttg agt aat tat tcc atc ata gac aaa ctt gtg aat ata gtg gat gac             1010
Leu Ser Asn Tyr Ser Ile Ile Asp Lys Leu Val Asn Ile Val Asp Asp
    300                 305                 310 ctt gtg gag tgc gtg aaa gaa aac tca tct aag gat cta aaa aaa tca             1058
Leu Val Glu Cys Val Lys Glu Asn Ser Ser Lys Asp Leu Lys Lys Ser
315                 320                 325                 330 ttc aag agc cca gaa ccc agg ctc ttt act cct gaa gaa ttc ttt aga             1106
Phe Lys Ser Pro Glu Pro Arg Leu Phe Thr Pro Glu Glu Phe Phe Arg
                335                 340                 345
```

-continued

```
att ttt aat aga tcc att gat gcc ttc aag gac ttt gta gtg gca tct      1154
Ile Phe Asn Arg Ser Ile Asp Ala Phe Lys Asp Phe Val Val Ala Ser
        350                 355                 360 gaa act agt gat tgt gtg gtt tct tca aca tta agt cct gag aaa gat      1202
Glu Thr Ser Asp Cys Val Val Ser Ser Thr Leu Ser Pro Glu Lys Asp
365                 370                 375 tcc aga gtc agt gtc aca aaa cca ttt atg tta ccc cct gtt gca tag      1250
Ser Arg Val Ser Val Thr Lys Pro Phe Met Leu Pro Pro Val Ala
    380                 385                 390 ctcgag                                                                1256

<210> SEQ ID NO 5
<211> LENGTH: 1256
<212> TYPE: DNA
<213> ORGANISM: Artificial Sequence
<220> FEATURE:
<223> OTHER INFORMATION: cDNA encoding a fusion protein of human CAR and
      mouse SCF with an artificial linker sequence

<400> SEQUENCE: 5
aagcttccac c atg gcg ctc ctg ctg tgc ttc gtg ctc ctg tgc gga gta        50
             Met Ala Leu Leu Leu Cys Phe Val Leu Leu Cys Gly Val
                             -15                 -10 gtg gat ttc gcc aga agt ttg agt atc act act cct gaa gag atg att       98
Val Asp Phe Ala Arg Ser Leu Ser Ile Thr Thr Pro Glu Glu Met Ile
         -5              -1   1               5                  10 gaa aaa gcc aaa ggg gaa act gcc tat ctg cca tgc aaa ttt acg ctt      146
Glu Lys Ala Lys Gly Glu Thr Ala Tyr Leu Pro Cys Lys Phe Thr Leu
                15                  20                  25 agt ccc gaa gac cag gga ccg ctg gac atc gag tgg ctg ata tca cca      194
Ser Pro Glu Asp Gln Gly Pro Leu Asp Ile Glu Trp Leu Ile Ser Pro
            30                  35                  40 gct gat aat cag aag gtg gat caa gtg att att tta tat tct gga gac      242
Ala Asp Asn Gln Lys Val Asp Gln Val Ile Ile Leu Tyr Ser Gly Asp
        45                  50                  55 aaa att tat gat gac tac tat cca gat ctg aaa ggc cga gta cat ttt      290
Lys Ile Tyr Asp Asp Tyr Tyr Pro Asp Leu Lys Gly Arg Val His Phe
60                  65                  70 acg agt aat gat ctc aaa tct ggt gat gca tca ata aat gta acg aat      338
Thr Ser Asn Asp Leu Lys Ser Gly Asp Ala Ser Ile Asn Val Thr Asn
75                  80                  85                  90 tta caa ctg tca gat att ggc aca tat cag tgc aaa gtg aaa aaa gct      386
Leu Gln Leu Ser Asp Ile Gly Thr Tyr Gln Cys Lys Val Lys Lys Ala
                95                  100                 105 cct ggt gtt gca aat aag aag att cac ctg gta gtt ctt gtt aag cct      434
Pro Gly Val Ala Asn Lys Lys Ile His Leu Val Val Leu Val Lys Pro
            110                 115                 120 tca ggt gcg aga tgt tac gtt gat gga tct gaa gaa att gga agt gac      482
Ser Gly Ala Arg Cys Tyr Val Asp Gly Ser Glu Glu Ile Gly Ser Asp
        125                 130                 135 ttt aag ata aaa tgt gaa cca aaa gaa ggt tca ctt cca tta cag tat      530
Phe Lys Ile Lys Cys Glu Pro Lys Glu Gly Ser Leu Pro Leu Gln Tyr
    140                 145                 150 gag tgg caa aaa ttg tct gac tca cag aaa atg ccc act tca tgg tta      578
Glu Trp Gln Lys Leu Ser Asp Ser Gln Lys Met Pro Thr Ser Trp Leu
155                 160                 165                 170 gca gaa atg act tca tct gtt ata tct gta aaa aat gcc tct tct gag      626
Ala Glu Met Thr Ser Ser Val Ile Ser Val Lys Asn Ala Ser Ser Glu
                175                 180                 185 tac tct ggg aca tac agc tgt aca gtc aga aac aga gtg ggc tct gat      674
Tyr Ser Gly Thr Tyr Ser Cys Thr Val Arg Asn Arg Val Gly Ser Asp
```

-continued

```
                    190                 195                 200
cag tgc ctg ttg cgt cta aac gtt gtc cct cct tca aat aaa gct cat      722
Gln Cys Leu Leu Arg Leu Asn Val Val Pro Pro Ser Asn Lys Ala His
        205                 210                 215 cat cac cat cac cat agc gct tcc gcc tct gct aag gag atc tgc ggg      770
His His His His His Ser Ala Ser Ala Ser Ala Lys Glu Ile Cys Gly
        220                 225                 230 aat cct gtg act gat aat gta aaa gac att aca aaa ctg gtg gca aat      818
Asn Pro Val Thr Asp Asn Val Lys Asp Ile Thr Lys Leu Val Ala Asn
235                 240                 245                 250 ctt cca aat gac tat atg ata acc ctc aac tat gtc gcc ggg atg gat      866
Leu Pro Asn Asp Tyr Met Ile Thr Leu Asn Tyr Val Ala Gly Met Asp
                    255                 260                 265 gtt ttg cct agt cat tgt tgg cta cga gat atg gta ata caa tta tca      914
Val Leu Pro Ser His Cys Trp Leu Arg Asp Met Val Ile Gln Leu Ser
                    270                 275                 280 ctc agc ttg act act ctt ctg gac aag ttc tca aat att tct gaa ggc      962
Leu Ser Leu Thr Thr Leu Leu Asp Lys Phe Ser Asn Ile Ser Glu Gly
        285                 290                 295 ttg agt aat tac tcc atc ata gac aaa ctt ggg aaa ata gtg gat gac      1010
Leu Ser Asn Tyr Ser Ile Ile Asp Lys Leu Gly Lys Ile Val Asp Asp
        300                 305                 310 ctc gtg tta tgc atg gaa gaa aac gca ccg aag aat ata aaa gaa tct      1058
Leu Val Leu Cys Met Glu Glu Asn Ala Pro Lys Asn Ile Lys Glu Ser
315                 320                 325                 330 ccg aag agg cca gaa act aga tcc ttt act cct gaa gaa ttc ttt agt      1106
Pro Lys Arg Pro Glu Thr Arg Ser Phe Thr Pro Glu Glu Phe Phe Ser
                    335                 340                 345 att ttc aat aga tcc att gat gcc ttt aag gac ttt atg gtg gca tct      1154
Ile Phe Asn Arg Ser Ile Asp Ala Phe Lys Asp Phe Met Val Ala Ser
                    350                 355                 360 gac act agt gac tgt gtg ctc tct tca aca tta ggt ccc gag aaa gat      1202
Asp Thr Ser Asp Cys Val Leu Ser Ser Thr Leu Gly Pro Glu Lys Asp
        365                 370                 375 tcc aga gtc agt gtc aca aaa cca ttt atg tta ccc cct gtt gca tag c    1251
Ser Arg Val Ser Val Thr Lys Pro Phe Met Leu Pro Pro Val Ala
        380                 385                 390 tcgag                                                                1256
```

<210> SEQ ID NO 6
<211> LENGTH: 1499
<212> TYPE: DNA
<213> ORGANISM: Artificial Sequence
<220> FEATURE:
<223> OTHER INFORMATION: cDNA encoding a fusion protein of human CAR and
    a single chain Fv derived from mouse monoclonal antibody against
    human CD34 with an artificial linker sequence

<400> SEQUENCE: 6

```
aagcttccac c atg gcg ctc ctg ctg tgc ttc gtg ctc ctg tgc gga gta       50
            Met Ala Leu Leu Leu Cys Phe Val Leu Leu Cys Gly Val
                        -15                 -10 gtg gat ttc gcc aga agt ttg agt atc act act cct gaa gag atg att       98
Val Asp Phe Ala Arg Ser Leu Ser Ile Thr Thr Pro Glu Glu Met Ile
-5                  -1  1                   5                   10 gaa aaa gcc aaa ggg gaa act gcc tat ctg cca tgc aaa ttt acg ctt       146
Glu Lys Ala Lys Gly Glu Thr Ala Tyr Leu Pro Cys Lys Phe Thr Leu
                15                  20                  25 agt ccc gaa gac cag gga ccg ctg gac atc gag tgg ctg ata tca cca       194
Ser Pro Glu Asp Gln Gly Pro Leu Asp Ile Glu Trp Leu Ile Ser Pro
            30                  35                  40
```

| | | |
|---|---|---|
| gct gat aat cag aag gtg gat caa gtg att att tta tat tct gga gac<br>Ala Asp Asn Gln Lys Val Asp Gln Val Ile Ile Leu Tyr Ser Gly Asp<br>          45                  50                          55 | 242 |
| aaa att tat gat gac tac tat cca gat ctg aaa ggc cga gta cat ttt<br>Lys Ile Tyr Asp Asp Tyr Tyr Pro Asp Leu Lys Gly Arg Val His Phe<br>60                      65                        70 | 290 |
| acg agt aat gat ctc aaa tct ggt gat gca tca ata aat gta acg aat<br>Thr Ser Asn Asp Leu Lys Ser Gly Asp Ala Ser Ile Asn Val Thr Asn<br>75                      80                      85                      90 | 338 |
| tta caa ctg tca gat att ggc aca tat cag tgc aaa gtg aaa aaa gct<br>Leu Gln Leu Ser Asp Ile Gly Thr Tyr Gln Cys Lys Val Lys Lys Ala<br>                  95                      100                    105 | 386 |
| cct ggt gtt gca aat aag aag att cac ctg gta gtt ctt gtt aag cct<br>Pro Gly Val Ala Asn Lys Lys Ile His Leu Val Val Leu Val Lys Pro<br>              110                    115                    120 | 434 |
| tca ggt gcg aga tgt tac gtt gat gga tct gaa gaa att gga agt gac<br>Ser Gly Ala Arg Cys Tyr Val Asp Gly Ser Glu Glu Ile Gly Ser Asp<br>          125                    130                    135 | 482 |
| ttt aag ata aaa tgt gaa cca aaa gaa ggt tca ctt cca tta cag tat<br>Phe Lys Ile Lys Cys Glu Pro Lys Glu Gly Ser Leu Pro Leu Gln Tyr<br>140                    145                    150 | 530 |
| gag tgg caa aaa ttg tct gac tca cag aaa atg ccc act tca tgg tta<br>Glu Trp Gln Lys Leu Ser Asp Ser Gln Lys Met Pro Thr Ser Trp Leu<br>155                    160                    165                    170 | 578 |
| gca gaa atg act tca tct gtt ata tct gta aaa aat gcc tct tct gag<br>Ala Glu Met Thr Ser Ser Val Ile Ser Val Lys Asn Ala Ser Ser Glu<br>              175                    180                    185 | 626 |
| tac tct ggg aca tac agc tgt aca gtc aga aac aga gtg ggc tct gat<br>Tyr Ser Gly Thr Tyr Ser Cys Thr Val Arg Asn Arg Val Gly Ser Asp<br>                190                    195                    200 | 674 |
| cag tgc ctg ttg cgt cta aac gtt gtc cct cct tca aat aaa gct cat<br>Gln Cys Leu Leu Arg Leu Asn Val Val Pro Pro Ser Asn Lys Ala His<br>          205                    210                    215 | 722 |
| cat cac cat cac cat agc gct tcc gcc tct gcc cag gtg cag ctg aag<br>His His His His His Ser Ala Ser Ala Ser Ala Gln Val Gln Leu Lys<br>220                    225                    230 | 770 |
| cag tca ggc cct ggc cta gtg cag ccc tca cag agc ctg tcc ttc atc<br>Gln Ser Gly Pro Gly Leu Val Gln Pro Ser Gln Ser Leu Ser Phe Ile<br>235                    240                    245                    250 | 818 |
| tgc aca gtc tct ggt ttc tca tta act agt cat ggt gta cac tgg gtt<br>Cys Thr Val Ser Gly Phe Ser Leu Thr Ser His Gly Val His Trp Val<br>              255                    260                    265 | 866 |
| cgc cag tct cca gga aag ggt ctg gag tgg ctg gga gtg ata tgg ggt<br>Arg Gln Ser Pro Gly Lys Gly Leu Glu Trp Leu Gly Val Ile Trp Gly<br>          270                    275                    280 | 914 |
| gct gga agg aca gac tat aat gca gct ttc ata tcc aga ctg agc atc<br>Ala Gly Arg Thr Asp Tyr Asn Ala Ala Phe Ile Ser Arg Leu Ser Ile<br>              285                    290                    295 | 962 |
| agc agg gac att tcc aag agc caa gtt ttc ttt aag atg aac agt ctg<br>Ser Arg Asp Ile Ser Lys Ser Gln Val Phe Phe Lys Met Asn Ser Leu<br>300                    305                    310 | 1010 |
| caa gtt gat gac aca gcc ata tat tac tgt gcc aga aat agg tac gag<br>Gln Val Asp Asp Thr Ala Ile Tyr Tyr Cys Ala Arg Asn Arg Tyr Glu<br>315                    320                    325                    330 | 1058 |
| agc tac ttt gac tac tgg ggc caa ggc acc acg gtc acc gtc tcc tca<br>Ser Tyr Phe Asp Tyr Trp Gly Gln Gly Thr Thr Val Thr Val Ser Ser<br>              335                    340                    345 | 1106 |
| ggt gga ggc ggt tca ggc gga ggt ggc tct ggc ggt ggc gga tcg gac<br>Gly Gly Gly Gly Ser Gly Gly Gly Gly Ser Gly Gly Gly Gly Ser Asp | 1154 |

-continued

|  |  |  |  |  |  |  |  |  | 350 |  |  |  |  | 355 |  |  |  |  | 360 |  |  |  |
|---|---|---|---|---|---|---|---|---|---|---|---|---|---|---|---|---|---|---|---|---|---|---|

```
atc gag ctc act cag tct cca ctc tcc ctg cct gtc agt ctt gga gat      1202
Ile Glu Leu Thr Gln Ser Pro Leu Ser Leu Pro Val Ser Leu Gly Asp
            365                 370                 375 cag gcc tcc atc tct tgc aga tct agt cag aac ctt gta cac agt aat      1250
Gln Ala Ser Ile Ser Cys Arg Ser Ser Gln Asn Leu Val His Ser Asn
        380                 385                 390 gga aat acc tat tta cat tgg tac ctg cag aag cca ggc cag tct cca      1298
Gly Asn Thr Tyr Leu His Trp Tyr Leu Gln Lys Pro Gly Gln Ser Pro
395                 400                 405                 410 aat ctc ctg atc tac aaa gtt tcc aac cga ttt tct ggg gtc cca gac      1346
Asn Leu Leu Ile Tyr Lys Val Ser Asn Arg Phe Ser Gly Val Pro Asp
                415                 420                 425 agg ttc agt ggc agt gga tca ggg aca gaa ttc aca ctc aag atc agc      1394
Arg Phe Ser Gly Ser Gly Ser Gly Thr Glu Phe Thr Leu Lys Ile Ser
            430                 435                 440 aga gtg gag gct gag gat ctg gga gtt tat ttc tgc tct caa agt aca      1442
Arg Val Glu Ala Glu Asp Leu Gly Val Tyr Phe Cys Ser Gln Ser Thr
        445                 450                 455 cat gtt ccg ctc acg ttc ggt gct ggg acc aag gtg gag ctg aaa cgg      1490
His Val Pro Leu Thr Phe Gly Ala Gly Thr Lys Val Glu Leu Lys Arg
    460                 465                 470 tagctcgag                                                             1499
```

<210> SEQ ID NO 7
<211> LENGTH: 28
<212> TYPE: DNA
<213> ORGANISM: Artificial Sequence
<220> FEATURE:
<223> OTHER INFORMATION: a forward PCR primer used in example 1

<400> SEQUENCE: 7
ccaagcttcc accatggcgc tcctgctg        28

<210> SEQ ID NO 8
<211> LENGTH: 44
<212> TYPE: DNA
<213> ORGANISM: Artificial Sequence
<220> FEATURE:
<223> OTHER INFORMATION: a reverse PCR primer used in example 1

<400> SEQUENCE: 8
agcgctatgg tgatggtgat gatgagcttt atttgaagga ggga        44

<210> SEQ ID NO 9
<211> LENGTH: 38
<212> TYPE: DNA
<213> ORGANISM: Artificial Sequence
<220> FEATURE:
<223> OTHER INFORMATION: a forward PCR primer used in example 1

<400> SEQUENCE: 9
agcgcttccg cctctgccga agggatctgc aggaatcg        38

<210> SEQ ID NO 10
<211> LENGTH: 29
<212> TYPE: DNA
<213> ORGANISM: Artificial Sequence
<220> FEATURE:
<223> OTHER INFORMATION: a reverse PCR primer used in example 1

<400> SEQUENCE: 10
ctcgagctat gcaacagggg gtaacataa        29

-continued

```
<210> SEQ ID NO 11
<211> LENGTH: 38
<212> TYPE: DNA
<213> ORGANISM: Artificial Sequence
<220> FEATURE:
<223> OTHER INFORMATION: a forward PCR primer used in example 1

<400> SEQUENCE: 11
agcgcttccg cctctgccaa ggagatctgc gggaatcc                           38

<210> SEQ ID NO 12
<211> LENGTH: 36
<212> TYPE: DNA
<213> ORGANISM: Artificial Sequence
<220> FEATURE:
<223> OTHER INFORMATION: a forward PCR primer used in example 1

<400> SEQUENCE: 12
agcgcttccg cctctgccca ggtgcagctg aagcag                             36

<210> SEQ ID NO 13
<211> LENGTH: 29
<212> TYPE: DNA
<213> ORGANISM: Artificial Sequence
<220> FEATURE:
<223> OTHER INFORMATION: a reverse PCR primer used in example 1

<400> SEQUENCE: 13
ctcgagctac cgtttcagct ccaccttgg                                     29
```

AGENTS FOR ADSORPTION AND BRIDGING FOR ADENOVIRUS

This nonprovisional application claims priority under 35 U.S.C. § 119(a) on Patent Application No. 2001-317766 filed in Japan on Oct. 16, 2001, which is herein incorporated by reference.

FIELD OF THE INVENTION

The present invention relates to technologies for adenoviral vector-mediated gene transfer to undifferentiated blood cells.

BACKGROUND OF THE INVENTION

Adenoviral vectors transiently exhibit high efficiency of gene transfer and expression as a vector for introducing genes into mammalian cells. They, furthermore, allow gene transfer to non-dividing cells and enable expression through administration to animal subjects, therefore, they have been developed as vectors for gene therapy (Breyer et al., Current Gene Therapy, Vol. 1, pp. 149–162). Although it is known that the adenoviral vectors have wide host range, the efficiency of gene transfer with regard to blood cells is low (Marini III et al., Cancer Gene Therapy, Vol. 7, pp. 816–825).

Infection of adenovirus into cells is thought to be a process consisting of two-stages: adsorption and internalization. It is thought that human adenovirus type 5 used as a vector, is adsorbed to a cell due to binding between a fiber of the virus and a cell surface protein, CAR (coxsackievirus adenovirus receptor) (Bergelson et al., Science, Vol. 275, 1320–1323), and then it is internalized into the cell due to binding between a penton base of the virus and cell surface proteins, integrins (Wickham et al., Cell, Vol. 73, pp. 309–319). The efficiency of adenoviral vector-mediated gene transfer is dependent on the intensity of the CAR expression of the target cells. However, CAR expression of blood cells is generally low, and in particular, it has been shown that undifferentiated blood cells, CD34 positive and CD38 negative cells hardly express CAR at all (Rebel et al., Stem Cells, Vol. 18, pp. 176–182). Further, a separate report (Leon et al., Proc. Natl. Acad. Sci. USA, Vol. 95, pp. 13159–13164) indicates that with lymphocytes that are forced to express CAR, the efficiency of adenoviral vector-mediated gene transfer improves. Therefore, the problem of the low efficiency of gene transfer to blood cells is caused by difficulty in adsorption of the virus to the cells. Increasing adsorption is an important technical target for improving efficiency of adenoviral vector-mediated gene transfer to blood cells, and various approaches directed to this object have been reported.

Smith et al. reported that they prepared a specific host-retargeting adenoviral vector by binding a ligand molecule being any one of SCF (stem cell factor), anti-c-Kit antibody, anti-CD34 antibody, anti-CD44 antibody or IL-2 to an adenovirus particle using avidin-biotin binding method, and that the modified vectors were improved in the efficiency of gene transfer to blood cells that expressed these specific receptors (Proc. Natl. Acad. Sci. USA, Vol. 96, pp. 8855–8860). However, according to the report of Smith et al., with M07e cells infected by this method with luciferase or GFP (green fluorescent protein) as a reporter gene, 95% positive cells were detected by PCR (polymerase chain reaction) on the virus genome DNA, but in the case of detection of the level of expression of GFP protein by flow cytometer, positive cells were slightly less that 20%, and it has been pointed out that there is a problem with internalization of the virus or in the expression stage of the virus genome.

Shayakhmetov et al. (J. Virol., Vol. 74, pp. 2567–2583) and Yotnda et al. (Gene Therapy, Vol. 8, pp. 930–937) reported that they substituted only fibers of an adenovirus type 5 vector with those of adenovirus type 35, developing an Ad5/F35 vector having different tropism to that of adenovirus type 5, and that the Ad5/F35 vector was improved in the efficiency of gene transfer to blood cells. This method requires a virus genome to be newly prepared, and it should be noted that a receptor molecule of adenovirus type 35 has not been identified. Thus, there is the problem that safety or pathogenicity in respect of human adenovirus type 35 has not been clarified.

On the other hand, there have been reports that gene transfer to blood cells is possible even where an ordinary adenovirus vector is used without carrying out any special modifications. (Watanabe et al., Blood, Vol. 87, pp. 5032–5039; Neering et al., Blood, Vol. 88, pp. 1147–1155; Takahashi et al, Blood, Vol. 91, pp. 4509–4515; Fan et al., Hum. Gene Ther, Vol. 11, pp. 1313–1327). In these reports, virus infection was performed at a high MOI (multiplicity of infection) of 100–500 and over a long period of 24 to 48 hours, and cell adsorption of the virus is thought to be non-specific (Marini III$^{rd}$ et al., Cancer Gene Therapy, Vol. 7, pp. 816–825). General adenovirus vector infection conditions are around 2 hours at about MOI 50, however, it is well known that adenovirus infection at a high concentration causes cytotoxicity, and it has been shown that toxicity is high particularly for undifferentiated blood cells (MacKenzie et al., Blood, Vol. 96, pp. 100–108).

Further, to promote introduction of genes into the target cells of nucleic acid delivery vehicles such as virus vectors, etc., there has been disclosed a complex construct of (1) a molecule which binds to the nucleic acid delivery vehicle and (2) a molecule which binds to the surface molecules of target cells linked by (3) a linker (O'Riordan et al., WO99/40214 and U.S. Pat. No. 6,287,857). In a concrete example of this, a complex construct can be used in which antibodies or peptides having binding activity corresponding to each of the nucleic acid delivery vehicles are chemically bound to surface molecules of target cells. Because the method of producing this complex construct involves chemically binding two different peptides using a coupling reagent, there are thought to be problems such as low product yield and non-uniform structure of the products.

There has also been reported a method that uses a polypeptide consisting of two constituent factors, an extracellular portion of CAR protein and a soluble ligand having affinity for target cells, as an agent to assist adsorption. Dmitriev et al. prepared a fusion polypeptide of CAR and epidermal growth factor, EGF, and reported that this polypeptide promotes infection of adenovirus to tumor cells expressing EGF receptor (J. Virol, Vol. 74, pp. 6875–6884). Further, Ebbinghaus et al. prepared a fusion polypeptide of CAR and human immunoglobulin Fc region, and reported promotion of infection of adenovirus to cells expressing Fcγ receptor (J. Virol, Vol. 75, pp. 480–489). However, neither EGF receptor nor Fcγ receptor is expressed in undifferentiated blood cells, and these fusion polypeptides cannot be applied to undifferentiated blood cells.

Therefore, there is a need to provide a specific adsorption agent for adenovirus 5 to undifferentiated blood cells that allows virus infection at an MOI that does not impart toxicity to undifferentiated blood cells, without requiring

SUMMARY OF THE INVENTION

The present inventors constructed an expression vector for the polypeptide of the present invention by the method described in Example 1; produced the polypeptide using animal cells according to the method described in Example 2; detected the polypeptide by the method described in Example 3; purified the polypeptide by the method described in Example 4; performed adenovirus vector infection to undifferentiated blood cells under conditions of presence/absence of the polypeptide according to the method described in Example 5; evaluated the effect of the polypeptide on efficiency of gene introduction with a flow cytometer according to the method described in Example 6, and observed that there was, in the presence of the polypeptide, a dramatic increase in fluorescence intensity and the ratio of positive cells where green fluorescent protein gene was used as a reporter gene. This indicated that the polypeptide solved the above-described problem thereby completing the present invention. That is to say, the present invention is directed to solving the problem by providing a linked polypeptide essentially consisting of a polypeptide having specific affinity for adenovirus and a polypeptide having specific affinity for undifferentiated blood cells. There have been no reports of using a polypeptide as an adsorption agent and promoting gene introduction by type 5 adenoviral vector to undifferentiated blood cells, and this technology was first accomplished by the present invention. A linked polypeptide essentially consisting of SCF and an extracellular region polypeptide of CAR protein, which is an aspect of the present invention, not only promotes gene introduction by type 5 adenoviral vector to undifferentiated blood cells, but has a proliferative action on undifferentiated blood cells, and a polypeptide having such an action is first provided by the present invention.

That is to say, the present invention encompasses the following inventions:

(1) A polypeptide comprising a polypeptide having affinity for a cell surface protein that is specifically expressed in undifferentiated blood cells which is joined to an extracellular region polypeptide of CAR protein.

(2) The polypeptide according to (1) above, wherein the polypeptide having affinity for a cell surface protein that is specifically expressed in undifferentiated blood cells, has an activity of stimulating proliferation of undifferentiated blood cells.

(3) The polypeptide according to (2) above, wherein the polypeptide having affinity for a cell surface protein that is specifically expressed in undifferentiated blood cells is SCF.

(4) The polypeptide according to (1) above, wherein the polypeptide having affinity for a cell surface protein that is specifically expressed in undifferentiated blood cells is a single chain anti-CD34 antibody.

(5) The polypeptide according to (3) above, which has the amino acid sequence represented in SEQ ID NO:1 of the sequence listing.

(6) The polypeptide according to (3) above, which has the amino acid sequence represented in SEQ ID NO:2 of the sequence listing.

(7) The polypeptide according to (4) above, which has the amino acid sequence represented in SEQ ID NO:3 of the sequence listing.

(8) A bridging agent for adsorption of adenovirus to an undifferentiated blood cell, which comprises the polypeptide according to any one of (1) to (7) above.

(9) The bridging agent according to (8) above, wherein the adenovirus is a vector for gene introduction.

(10) A nucleic acid delivery vehicle comprising the polypeptide according to any one of (1) to (7) above, and a recombinant adenovirus vector.

The sequences listed in the Sequence Listing are explained below. SEQ ID NO: 1 is an amino acid sequence of a polypeptide consisting of an extracellular region of human CAR protein linked with an extracellular region of human SCF protein. Amino acid Nos. 1 to 217 correspond to the extracellular region of human CAR protein and Nos. 230 to 393 correspond to the extracellular region of human SCF protein. SEQ ID NO: 2 is an amino acid sequence of a polypeptide consisting of an extracellular region of human CAR protein linked with an extracellular region of mouse SCF protein. Amino acid Nos. 1 to 217 correspond to the extracellular region of human CAR protein and Nos. 230 to 393 correspond to the extracellular region of mouse SCF protein. SEQ ID NO: 3 is an amino acid sequence of a polypeptide consisting of an extracellular region of human CAR protein linked with a single chain anti-CD34 antibody. Amino acid Nos. 1 to 217 correspond to the extracellular region of human CAR protein, and Nos. 230 to 474 correspond to single chain anti-CD34 antibody. SEQ ID NO:4 is a DNA sequence comprising a DNA sequence encoding the amino acid sequence according to SEQ ID NO: 1 of a polypeptide consisting of an extracellular region of human CAR protein linked with an extracellular region of human SCF protein. SEQ ID NO:5 is a DNA sequence comprising a DNA sequence encoding the amino acid sequence according to SEQ ID NO:2 of a polypeptide consisting of an extracellular region of human CAR protein linked with an extracellular region of mouse SCF protein. SEQ ID NO: 6 is a DNA sequence comprising a DNA sequence encoding the amino acid sequence according to SEQ ID NO:3 of a polypeptide consisting of an extracellular region of human CAR protein linked with a single chain anti-CD34 antibody. SEQ ID NOS:7–13 are DNA sequences of PCR primers used in the Examples.

The contents described in the description and drawings of Japanese Patent Application No. 2001-317766, which forms the basis of a claim to priority for the present application, are incorporated herein in their entirety.

1. shows a polypeptide consisting of a CAR extracellular region and a SCF extracellular region linked by a linker.
2. shows a polypeptide consisting of a CAR extracellular region and an anti-human CD34 single chain antibody (My10 scFv) linked by a linker.
3. shows an immunoglobulin-type polypeptide having a CAR extracellular region and an affinity region for undifferentiated blood cells.

Abbreviations: L (linker), scFv (single chain antibody), Fc (crystalline fragment)

Figure 2:
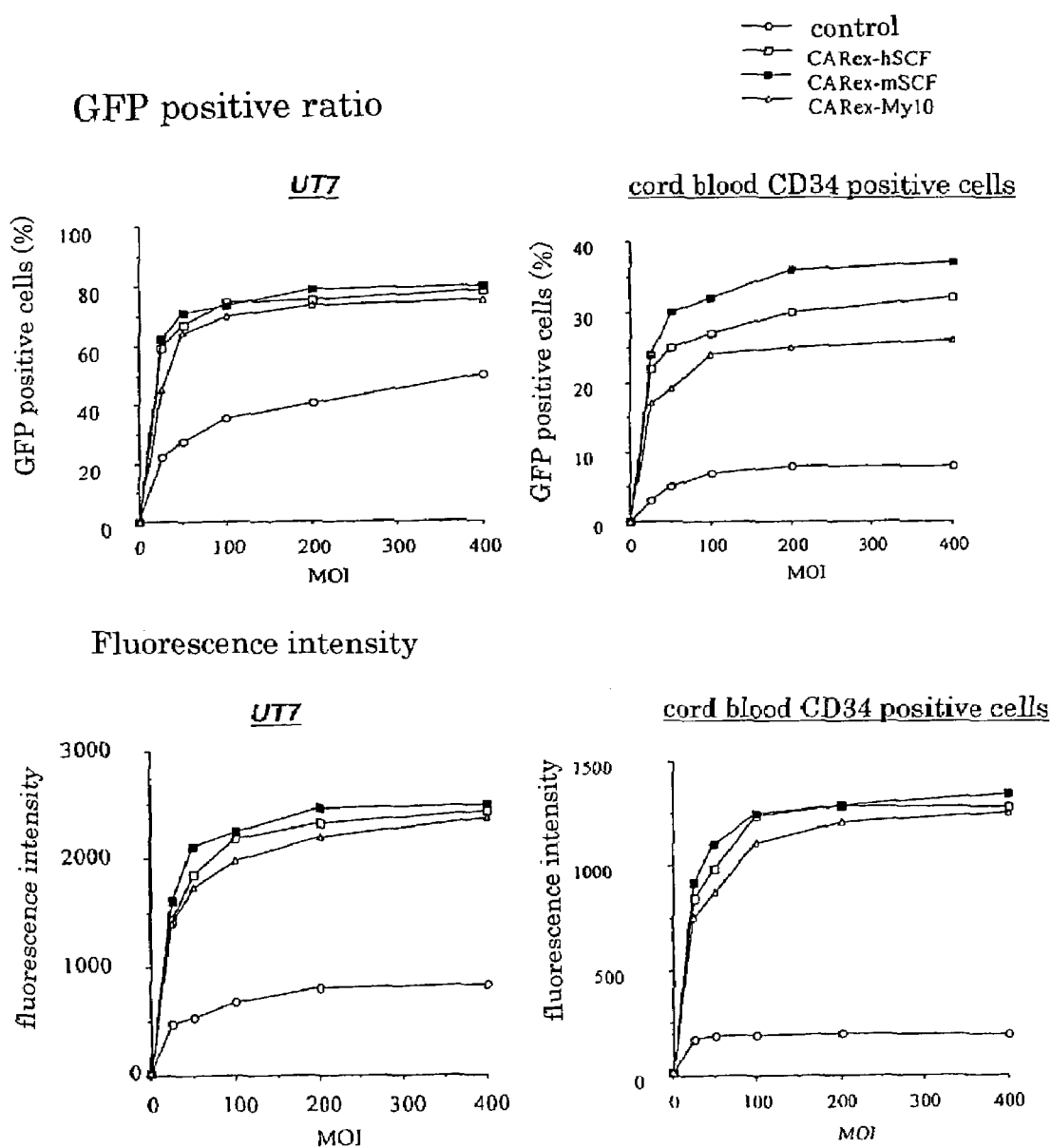

FIG. 2 indicates, by ratio of GFP positives and fluorescence intensity, the effect of the polypeptide of the present invention on efficiency of adenovirus vector gene introduction to human undifferentiated blood cell line UT-7, and CD34 positive cells derived from human cord blood.

DETAILED DESCRIPTION OF THE INVENTION

Figure 1:
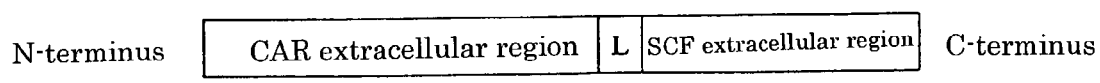
FIG. 1 is a schematic diagram of the polypeptide of the present invention.
Figure 1:
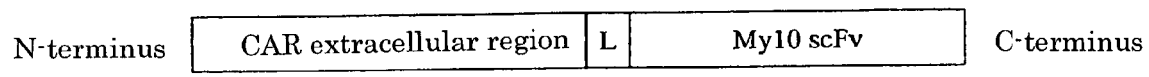
Figure 1:
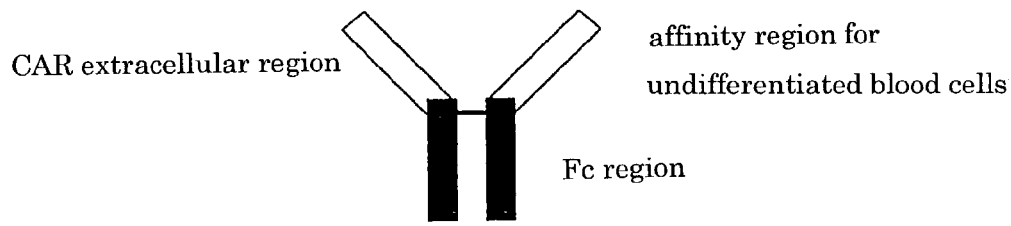

The polypeptide of the present invention is a polypeptide having two affinity regions: a region having affinity for a cell surface protein which is expressed specifically in undifferentiated blood cells and a CAR extracellular region having affinity for fiber of adenovirus, which mediates specific adsorption of adenovirus to undifferentiated blood cells. An example of this is schematically indicated in FIG. 1.

Undifferentiated blood cells are cells capable of differentiating into hemocytes such as erythrocytes, granulocytes, monocytes, lymphocytes and platelets, etc. It is known that undifferentiated blood cells are cells that do not express differentiation antigen, for example, Fcγ receptor or EGF receptor, and that there exists a cell surface protein that expresses specifically at an undifferentiated stage. Examples of such a cell surface protein include CD34, c-Kit(CD117), and AC133(CD133), etc. Examples of polypeptides having affinity for these cell surface proteins include SCF, which has affinity for c-Kit, L-selectin, which has affinity for CD34, and antibodies to cell surface protein, for example, single chain anti-CD34 antibody. Among these, SCF and antibodoies to CD34 have actually been clinically examined, and are particularly preferable. Further, a single chain antibody is a compact molecular form and has the merit that a chimeric protein can be readily prepared therewith. It should be noted that herein, the term "be expressed specifically" refers to expression only at the undifferentiated stage in blood cells derived from peripheral blood, bone marrow or cord blood; and that no expression, or almost no expression can be observed in differentiated cells. Further, herein, the term "has affinity" refers to the existence of high interaction through non-covalent bonds such as hydrogen bonds or hydrophobic bonds, etc. and energetically stable existence as a complex under certain conditions.

The CAR protein used in the present invention is not limited to that derived from humans. From the fact that mouse-derived CAR protein can also be an adenovirus receptor (Bergelson et al., J. Virol., Vol. 72, pp. 415–419), and also the fact that the amino acid sequences of human, mouse, rat, pig, and dog-derived CAR are well conserved (Fechner et al., Gene Ther., Vol. 6, pp. 1520–1535), CAR derived from a mammal, such as a human, mouse, rat, pig, dog, etc., can be suitably used regardless of species difference. However, particularly preferable are those derived from human or mouse. The present invention uses an extracellular region of this CAR protein.

The extracellular region of CAR protein has two immunoglobulin-like regions (Bergelson et al., Science Vol. 275, pp. 1320–1323). These immunoglobulin-like regions are designated D1 and D2 starting from the one closest to the amino terminus, and it has been shown that D1 alone is capable of binding with adenoviral fiber (Freimuth et al., J. Virol., Vol. 73, pp. 1392–1398). Therefore, it is a necessary condition of the extracellular region polypeptide of CAR protein used in the polypeptide of the present invention that it comprises at least D1, and it may comprise D2 and other regions. Note that details of the immunoglobulin-like region are described in Bork et al, J. Mol. Biol., Vol. 242, pp. 309–320. Examples of specific amino acid sequences of D1 and D2 are as follows: D1 corresponds to the 94 residues from amino acid No. 15, glycine, to No. 108, glycine in the amino acid sequences according to SEQ ID NOS: 1 to 3 in the Sequence Listing; and D2 corresponds to the 64 residues from amino acid No. 136, glycine, to No. 200, glycine, in the amino acid sequences according to SEQ ID NOS: 1 to 3 in the Sequence Listing.

FIG. 1-1 is an example of a fusion polypeptide of a CAR extracellular region and a SCF extracellular region linked by a linker. FIG. 1-2 is an example of a fusion polypeptide of CAR extracellular region and a single chain anti-CD34 antibody linked by a linker. These can be prepared according to the method described in the Examples. SEQ ID NOS: 1 and 2 in the Sequence Listing indicate examples of amino acid sequences of the fusion polypeptide shown in FIG. 1-1. Mouse SCF, like human SCF, has affinity for c-Kit (also referred to as CD117) which expresses in human undifferentiated blood cells, and can also be used as a region having affinity for a cell surface protein that expresses specifically in undifferentiated blood cells. SEQ ID NO:3 in the Sequence Listing shows an example of an amino acid sequence of the fusion peptide shown in FIG. 1-2. In the examples in FIGS. 1-1 and 1-2, the CAR extracellular region is shown on the amino terminal side, and a region having affinity for a cell surface protein that expresses specifically in undifferentiated blood cells is shown on the carboxyl terminal side of the polypeptide. However, this order can be reversed, and it is possible to arrange the region having affinity for a cell surface protein that expresses specifically in undifferentiated blood cells on the amino terminal side, and the CAR extracellular region of the carboxyl terminal side.

An example of a molecular tag that can be used in the present invention as shown in the Examples is the six (6) residues of histidine (corresponding to amino acid Nos. 218 to 223 in the polypeptide sequences according to SEQ ID NOS: 1–3 in Sequence Listing) that is inserted between the two affinity regions as a His tag. Molecular tags are not limited to His tag, and other tags where the relationship between the epitope sequence and the antibody which recognizes it is established such as FLAG, Myc, GST, and Fe region of immunoglobulin can be inserted (Fritze et al., Methods Enzymol., Vol. 327, pp. 3–16). The position of the molecular tag is not limited to between the two affinity regions, and it is possible to position the molecular tag at the amino terminal or the carboxy terminal of the polypeptide of the present invention. Further, because the arrangement of a molecular tag is only for the purpose of making it easier to detect and purify the polypeptide, it can be deleted.

A linker that can be used in the present invention, as Examples, is a linker sequence consisting of a six (6) residue repeated sequence of serine and alanine (corresponding to amino acid Nos. 224 to 229 in the polypeptide sequences according to SEQ ID NOS: 1–3 presented in the Sequence Listing). The linker sequence is then inserted between the two affinity regions. Further, as long as the linker has a sequence that does not interfere with the two affinity regions and does not affect the production or secretion of this polypeptide, the type of amino acids and length of the sequence are not an issue, but a preferable sequence has between 2 and 20 residues and does not include any known peptide motif.

Further, the DNA sequences indicated in the Examples according to SEQ ID NOS: 4–6 in the Sequence Listing include a DNA sequence encoding a wild type signal peptide of human CAR for the purpose of effecting secretion of the polypeptide in a medium. This corresponds to Nos. 12 to 68 in each of SEQ ID NO: 4–6. Because the signal peptide is not something that needs necessarily to be included in the polypeptide of the present invention, it can be substituted by another sequence having signal peptide activity. Further, in order to produce and accumulate the polypeptide within the cells, the signal peptide can be deleted but the initiation codon retained.

The present invention further allows the preparation of a immunoglobulin-like polypeptide having two different affinity regions by preparing DNA sequences encoding 2 types of Fc chimera polypeptide: a Fc chimera polypeptide in which the Fab region of immunoglobulin is substituted by (1) a polypeptide having affinity for a cell surface protein that expresses specifically in undifferentiated blood cells, and an Fc chimera polypeptide substituted by (2) an extracellular region of CAR protein; and then co-transducing these 2 types of DNA sequence into a protein-producing host cell. FIG. 1-3 is an example of an immunoglobulin-type polypeptide prepared in this manner that has affinity regions for CAR extracellular region and undifferentiated blood cells. Further, a polypeptide of a similar form can be prepared according to the method of Zuo et al. (Protein Engineering, Vol. 13, pp. 361–367).

Herein, the term "linked polypeptide", refers to a plurality of polypeptides existing as one complex under physiological conditions by means of covalent bonding, ionic bonding, hydrogen bonding, hydrophobic bonding, electrostatic bonding, hydrogen bonding via water molecules, van der Waals atraction, or these forces operating in concert. Preferably this term refers to a plurality of polypeptides existing as a single molecule by means of covalent bonding, and more preferably to a plurality of polypeptides existing as a single peptide chain through gene recombination.

Methods of producing a gene recombinant polypeptide include using expression in bacteria, of which *E. coli* is representative, in yeast and in insect cells in addition to expression in animal cells, as described in the Examples. This method is described in detail in Part 1 of *Tanpaku Jikken Protocol—1 Kinokaisekihen*, edited by Ono et al., Shujunsha. Further, production is also possible in an acellular protein synthesis system (Shimizu et al., Nature Biotechnology, Vol. 19, pp. 751–755), in silkworms (Wu et al., Protein Expr Purif, Vol. 21, pp. 192–200), and in the breast milk of animals (Ko et al., Transgenic Res., Vol. 9, pp. 215–222).

On the other hand, there is also a report that sugar chain of heparan sulphate glucosaminoglycans increase affinity in adsorption of adenovirus to cells (Dechecchi et al., J. Virol., Vol. 75, pp. 8772–8780). Therefore, as a method of producing the polypeptide, any of the above-described methods can be used, however, eukaryotic cells are preferable because of their property of adding sugar chains to polypeptides.

The polypeptide of the present invention enables introduction into undifferentiated blood cells of any gene incorporated into an adenoviral vector. Further c-Kit expresses not only in undifferentiated blood cells but also in other stem cells, and the polypeptide linked with SCF can be used with respect to such c-Kit positive cells. It is a feature of the adenoviral vector that it allows insertion of relatively large genes of up to about 33 kb, and when using the polypeptide of the present invention, there is no restriction on the gene, and it is possible to insert any gene. However, considering that one property of adenovirus vectors is that they allow transient gene expression in undifferentiated blood cells, examples exhibit particular utility would include expression of site-specific recombinase and a group of transcription factors relating lineage induction.

Site-specific recombinase such as Cre recombinase (Gorman et al., Curr. Opin. Biotechnol., Vol. 11, pp. 455–460) and Flp recombinase (Buchholz et al., Nat. Biotechnol., Vol. 16, pp. 657–662) is useful as a DNA recombinant technique in mammalian cells (Metzger et al., Curr. Opin. Biotechnol., Vol. 10, pp. 470–476), however intracellular expression of the gene in long term and large amounts is known to cause damage to the cellular genome DNA (Loonstra et al, Proc. Natl. Acad. Sci. USA, Vol. 98, pp. 9209–9214). Until now there had been no means by which to effect expression of site-specific recombinase transiently in undifferentiated blood cells. However, by using the polypeptide of the present invention, expression by adenovirus vector is possible and it is possible to perform DNA recombinant techniques intracellularly while minimizing damage to the cell genome.

Undifferentiated blood cells can differentiate into hemocytes such as erythrocytes, granulocytes, monocytes, lymphocytes, platelets, etc. and in recent years it has been reported that hematopoeitic stem cells which are a type of undifferentiated blood cells can differentiate into cells of different lines such as vascular endothelium (Jackson et al., J. Clin. Invest, Vol. 107, pp. 1–8), nervous cells (Eglitis et al., Proc. Natl. Acad. Sci. USA, Vol. 94, pp. 4080–4085), myocardium (Orlic et al., Nature, Vol. 410, pp. 701–705), skeletal muscle (Gussori et al., Nature, Vol. 401, pp. 390–394), biliary epithelial cells and hepatocytes (Lagasse et al., Nat. Med., Vol. 6, pp. 1229–1234). In these reports, hematopoeitic stem cells that have been transplanted in animals spontaneously differentiated into different lines in response to the in vivo environment, but no technique of arbitrarily inducing these cells into cells of different lines is known. On the other hand, it is known that intracellular expression of a group of transcription factors called "master genes", effects induction of embryonic cells into cells of specific lineages, for example, MyoD for muscle (Boukamp, Semin. Cell Biol., Vol. 6, pp. 157–163), SIM for nerve (Nambu et al., Cell, Vol. 67, pp. 1157–1167), Ikaros for lymphocyte (Molnar et al., Mol. Cell. Biol., Vol. 14, pp. 8292–8303), Cbfal for bone (Komori, Protein Nucleic Acid and Enzyme, Vol. 45, pp. 13–17), SCL for blood (Porcher et al., Cell, Vol. 86, pp. 47–57), and Pdx-1 for pancreas (Grapin-Botton et al., Genes Dev., Vol. 15, pp. 444–454), etc. Therefore, by incorporating these master genes into a adenoviral vector and using the polypeptide of the present invention, it can be used for induction into cells of any cells of different lines, by transiently introducing a gene into undifferentiated blood cells or c-Kit positive cells.

Further, Kyba et al. report that by forcedly expressing HoxB4 gene in embryonic stem cell (ES cell) or yolk sac hematopoeitic cells which are embryonic primitive hematopoeitic cells, it is possible to induce adult hematopoeitic stem cells (definitive adult hematopoeitic stem cell) which are capable of differentiating both lineages into lymphocytic and hematic cells (Kyba et al., Cell, Vol. 109, pp. 29–37, 2002). In this report, it is described that in order to induce adult hematopoeitic stem cells, constitutive expression of HoxB4 gene is not preferable, but rather transient expression is preferable. For this reason, Kyba et al. adopted a method involving introduction into cells of a retroviral vector whereby expression of HoxB4 gene can be transiently induced by tetracycline. The present inventors realized that adoption of adenoviral vector could be used to express HoxB4 transiently. ES cells, embryo-like bodies differentiated from ES cells, and yolk sac hematopoeitic cells each express c-Kit, and it is possible to infect the cells with an adenoviral vector enabling expression of HoxB4 gene by suitably using the polypeptide linked with c-Kit according to the present invention. Further, using this method, by effecting transient expression in cells of Hox genes other than HoxB4 enables induction of any group of cells. Example of Hox genes for this purpose include msx1 which induces muscle cells (Odelberg et al., Cell, Vol. 103, pp. 1099–1109, 2000).

EXAMPLES

The present invention is explained in more detail below by way of Examples. However, these Examples are for the purposes of explanation and should not be taken to limit the technical scope of the present invention. In the Examples below, gene manipulation techniques are ones ordinarily performed by persons skilled in the art. Experiments can be conducted in accordance with, for example, Molecular Cloning, A Laboratory Manual, Third Edition, 2001, Cold Spring Harbor Laboratory Press, edited by J. Sambrook and D. W. Russel et al.

It should be noted that for synthetic oligoDNA to be used as a PCR primer, the preparation of any sequence can be entrusted to an industry specialist, an example of which is Takara Shuzo Co., Ltd.

Example 1

Preparation of a Fusion Polypeptide Expression Vector

For cDNA encoding human CAR, human SCF, mouse SCF, expressed sequence tag (EST) clones respectively registered as GenBank Registration Nos. BE545085, BF675585, BF021525 were purchased from Invitrogen, and sequences confirmed with a DNA sequencer. For DNA encoding anti-human CD34 single chain antibody, plasmid pCANMY10 described in Japanese Patent Office Patent Publication (Unexamined Application) No. 10-155489 was obtained.

(i) A Fusion Protein of Human CAR and Human SCF Having an Artificial Linker Sequence Using synthetic oligoDNA primers, CAR1SHIND and CAR3AHISAOR, represented in SEQ ID NOS: 7 and 8 in the Sequence Listing, PCR was performed using the above human CAR cDNA clone as a template, and a PCR product of approximately 750 base pairs (bp) was obtained. This was sub-cloned into plasmid vector pCR2.1 (INVITROGEN), and it was confirmed that the PCR product was a DNA sequence having a recognition sequence of restriction enzyme Hind III on the 5'-side and a recognition sequence of restriction enzyme Aor51H I on the 3'-side of a DNA sequence encoding a polypeptide sequence having a 6-residue histidine (His tag) added to the C-terminal side of an extracellular region of human CAR comprising a signal peptide. This plasmid was designated pCR/CARex.

Using synthetic oligoDNA primers, HSCF1SLINK and HSCF2ASTOP, which are represented in SEQ ID NOS: 9 and 10 in the Sequence Listing, PCR was performed using the above human SCF cDNA clone as a template, and a PCR product of approximately 500 bp was obtained. This was sub-cloned into plasmid vector pCR2.1, and it was confirmed with a DNA sequencer that the PCR product had a DNA sequence adding a stop codon and a recognition sequence of restriction enzyme Xho I linked to the 3'-side of a DNA sequence encoding a polypeptide having a 6-residue linker sequence added to the N-terminal side of an extracellular region of human SCF. This plasmid was designated pCR/hSCF.

Next, ligation processing was performed with the following 3 DNA fragments (a) to (c): (a) an approximately 750 bp DNA fragment obtainable by digesting pCR/CARex with restriction enzymes, Hind III and Aor51H I, (b) an approximately 500 bp DNA fragment obtainable by digesting pCR/hSCF with restriction enzymes, Aor51H I and Xho I, and (c) an approximately 5.4 kilo base pairs (kb) DNA fragment obtainable by digesting pcDNA3.1(+) (INVITROGEN) with restriction enzymes, Hind III and Xho I. The thus obtained plasmid was digested with restriction enzymes, Hind III and Xho I, to confirm that the plasmid was constituted by DNA fragments of approximately 1.3 kb and approximately 5.4 kb. That is, it was confirmed that the plasmid construction was such that the DNA sequence encoding a fusion polypeptide of human CAR extracellular region and human SCF extracellular region linked by means of a His tag and a linker was inserted between the cytomegalovirus-derived promoter of pcDNA3.1(+) vector and bovine growth factor-derived poly(A) signal adding region and this plasmid was designated pcDNA/CARex-hSCF. The DNA sequence of the Hind III-Xho I fragment of pcDNA/CARex-hSCF, and the amino acid sequence encoded thereby are shown in SEQ ID NO: 4 in the Sequence Listing.

(ii) A Fusion Protein of Human CAR and Mouse SCF Having an Artificial Linker Sequence Using synthetic oligoDNA primers, MSCF1SLINK and HSCF2ASTOP, which are represented in SEQ ID NOS: 11 and 10 of the Sequence Listing, PCR was performed using a cDNA clone of the above-described mouse SCF as a template, and a PCR product of approximately 500 bp was obtained. This was subcloned into plasmid vector pCR2.1, and it was confirmed with a DNA sequencer that the PCR product was a DNA sequence having a stop codon and a recognition sequence of restriction enzyme Xho I linked to the 3'-side of a DNA sequence encoding a polypeptide having a 6-residue linker sequence added to the N-terminal side of an extracellular region of mouse SCF. This plasmid was designated pCR/mSCF.

Next, ligation processing was performed on the following three fragments: (d) an approximately 500 bp DNA fragment obtainable by digestion of pCR/mSCF with restriction enzymes, Aor51H I and Xho I, and the above fragments (a) and (c). The thus obtained plasmid was digested with restriction enzymes, Hind III and Xho I, to confirm that the plasmid was constituted by DNA fragments of approximately 1.3 kb and approximately 5.4 kb. That is, it was confirmed that the plasmid construction was such that the DNA sequence encoding a fusion polypeptide of human CAR extracellular region and mouse SCF extracellular region linked by means of a His tag and a linker was inserted between the cytomegalovirus-derived promoter of pcDNA3.1(+)vector and bovine growth factor-derived poly (A) signal adding region and this plasmid was designated pcDNA/CARex-mSCF. The DNA sequence of the Hind III-Xho I fragment of pcDNA/CARex-mSCF, and the amino acid sequence encoded thereby are shown in SEQ ID NO: 5 in the Sequence Listing.

(iii) A Fusion Protein of Human CAR Having an Artificial Linker Sequence, and Single Chain Fv Derived from Mouse Monoclonal Antibody Against Human CD34.

Using synthetic oligoDNA primers, MY1SLINK and MY2ATAGXHO, as represented in shown in SEQ ID NOS: 12 and 13 in the Sequence Listing, PCR was performed with the above plasmid pCANMY10 as a template, and a PCR product of approximately 760 bp was obtained. This was subcloned into plasmid vector pCR2.1 and it was confirmed with a DNA sequencer that the PCR product was a DNA sequence having a stop codon and recognition sequence of restriction enzyme Xho I linked to the 3'-side of a DNA sequence encoding a 6-base linker sequence of the 5'-side of a nucleic acid sequence consisting of nucleic acids Nos. 88 to 822 of SEQ ID NO:3 of Japanese Patent Publication (Unexamined Application) No. 10-155489 (corresponding to No. 756 to No. 1490 of SEQ ID NO: 6). This plasmid was designated pCR/My10. Next, (e) an approximately 760 bp DNA fragment obtainable by digesting pCR/My10 with restriction enzymes, Aor51H I and Xho I, was obtained, and ligation processing was performed on the three fragments, fragment (e) and the above-described fragments (a) and (c). The thus obtained plasmid was digested with restriction enzymes, Hind III and Xho I, confirming that the plasmid was constituted by DNA fragments of approximately 1.5 kb and approximately 5.4 kb, that is, confirming that the construction of the plasmid was such that the DNA sequence encoding a fusion peptide of human CAR extracellular region and anti-human CD34 single chain antibody linked by means of a His tag and linker, was inserted between a cytomegalovirus-derived promoter of pcDNA3.1(+) vector and the bovine growth factor-derived poly(A) signal additing region. This plasmid was designated pcDNA/CARex-My10. The DNA sequence of the Hind III-Xho I fragment of pcDNA/CARex-My10, and the amino acid sequence coded thereby are shown in SEQ ID NO: 6 in the Sequence Listing.

Example 2

Production of the Fusion Polypeptide In COS-7 Cells

Gene introduction into COS-7 cells (available from Riken Gene Bank) was performed respectively with plasmids pcDNA/CARex-hSCF, pcDNA/CARex-mSCF and pcDNA/CARex-My10 prepared in Example 1, and as a control, plasmid pcDNA3.1 having no insert, and polypeptides were produced. COS-7 cells ($5\times10^6$ cells) were cultured in 90 mm-diameter culture dishes (Falcon 3003) in 10 ml of Dulbecco's Modified Eagle medium (DME) containing 10% FCS (fetal calf serum) for 24 hours, at 37° C., in a 5% $CO_2$ incubator. As a gene introduction reagent, Lipofect Amine Plus (Gibco) was used. To 10 µl (1 µg/µl) of asceptic plasmid, 690 µl of DME was added, and further, 50 µl of PLUS reagent was added to produce Solution I. Next, 700 µl of DME was added to 50 µl of Lipofect Amine, to produce Solution II. Solution I was mixed with Solution II, and allowed to stand at room temperature for 15 minutes, and this was named Solution III. The cell medium was removed by suction, 5 ml of non-serum DME was added, and the total volume of Solution III was added, and mixed slowly. This was cultured in a 5% $CO_2$ incubator at 37° C., for 3 hours. Five milliliters of non-serum DME was added, and then cultivation was continued for a further 3 days. The culture supernatant was collected and debris removed by centrifugation-separation at 3000 rpm for 5 minutes. Further, filtration was performed with a 0.22 µm filter, and Ultrafree (Millipore) was used to perform buffer exchange with pH7.4 phosphate buffered physiological saline (PBS) and to concentrate by a factor of approximately 100.

Example 3

Detection of the Fusion Polypeptide

Detection of the fusion polypeptides was performed by Western blotting targeting the His tag. That is, 10 µl of the fusion polypeptide sample obtained in Example 2 was processed for 5 minutes at 100° C. in the presence of 2-mercaptoethanol to denature and reduce the protein, and SDS polyacrylamide gel electrophoresis was performed using a 5–15% concentration gradient gel. This was transferred to a nitrocellulose membrane (Hybond-ECL, Amersham Pharmacia Biotec) by performing electroblotting (Trans Blot SD, BioRad) at 15 Volt, for 15 minutes. Detection was performed by peroxidase-labeling His tag protein with Penta-His HRP Conjugate Kit (Qiagen) and detecting with ECL (Amersham Pharmacia Biotec). By comparing with the sample obtained by introduction of a control vector, polypeptide (CARex-hSCF), being CAR extracellular region linked with human SCF, and polypeptide (CARex-mSCF), being CAR extracellular region linked with mouse SCF, were both detected as specific bands at approximately 46 kD. Polypeptide (CARex-My10), being CAR extracellular region linked with anti-human CD34 single chain antibody, was detected as a specific band at approximately 52 kD. Thus, a method of producing the fusion polypeptide was established.

Example 4

Purification of the Fusion Polypeptide

A concentrated solution of the fusion polypeptide obtained in Example 2 was purified with His tag as a target. That is, to a 1 ml concentrated solution in a 1.5 ml microtube, 10 µl of nickel NTA magnetized agarose beads (Qiagen) was added, and mixed by tumbling in a shaker for 2 hours at 4° C. This was allowed to stand under strong magnetism for 1 minute, and then the supernatant was discarded. One milliliter of washing solution (50 mM $NaH_2PO_4$, 0.42M NaCl, 20 mM imidazole) was added and beads suspended. This was allowed to stand under strong magnetism for 1 minute, and then the supernatant was discarded. Washing was performed by this method three times, and 50 µl of extraction solution (50 mM $NaH_2PO_4$, 0.42M NaCl, 250 mM imidazole) was added, the beads suspended, and this was allowed to stand under strong magnetism for 1 minute, and then the supernatant collected. Ten microliters of the sample were processed in the presence of 2-mercaptoethanol for 5 minutes at 100° C., to denature/reduce the protein, SDS polyacrylamide gel electrophoresis was performed by using a 5–15% concentration gradient gel, and silver staining (Wako Pure Chemical Industries) was performed. CARex-hSCF and CARex-mSCF were both detected at approximately 46 kD, and CARex-My10 was detected as an almost pure single band at approximately 52 kD. Thus, a method of purifying the fusion polypeptide was established.

Example 5

Infection of Adenovirus to Undifferentiated Blood Cells

The gene introduction promoting effect of the fusion polypeptide was examined by infection experiments to c-Kit positive and CD34 positive human undifferentiated blood cell line UT-7 (available from Dr. Norio Komatu, at Jichi Medical School, Japan) or cord blood-derived CD34 positive cells, which are human undifferentiated blood cells (available from Biowhittaker) with adenoviral vector Ax1CAgfp (Available as Registration No. RDB1727, from Riken Genebank) which enables expression of green fluorescent protein (GFP). Propagation, purification and titer determination of the adenovirus vector was performed in accordance with the method of Kanegae et al. (Shin Idenshi Kougaku Handbook $3^{rd}$ Ed., pp. 202–209, Ed. By Muramatsu et al., Yodosha). UT-7 cells were pre-cultured in RPMI1640 medium (Gibco) having added 10 ng/ml of human GM-CSF (Peprotech) and 10% FCS (referred to herein as "growth medium"), at 37° C. in a 5% $CO_2$ incubator. With cord blood-derived CD34 positive cells, it was confirmed that live cells stained with trypan blue were 90% or more. UT-7 or cord blood-derived CD34 positive cells ($1 \times 10^5$ cells) were suspended in 0.1 ml of growth medium, apportioned on a 48-well plate (Falcon 3078). To each was added 5 μl of the concentrated solution of each of the various COS-7 culture supernatants obtainable in Example 2, and further Ax1CAgfp was added to establish an MOI of 0, 25, 50, 100, 200, or 400. After incubating for 2 hours, the cells and the medium were collected in a 1.5 ml microtube, and centrifuged at 5000 rpm, for 30 seconds. The supernatant was removed, 0.5 ml of a fresh growth medium was added, the cells suspended, and seeded on a fresh 48-well plate, and then further incubated for 16 hours.

Example 6

Detection of GFP Positive Cells by Flow Cytometer

Cells obtained in Example 5 were collected in a 1.5 ml microtube, and subjected to centrifugation at 6000 rmp, for 30 seconds. The supernatant was removed, and the cells were washed with PBS, then suspended in PBS containing 5 μg/ml of propidium iodide (PI) and 5% FCS. The cells were then transferred to a polystyrene small test tube (Falcon 2058), and allowed to stand on ice for 30 minutes. Using a flow cytometer, FACScan (Becton Dickinson), the cells were irradiated with 488 nm argon laser light, and GFP positive cells having a fluorescence maximum at 509 nm, were detected with FL1 and dead cells stained with PI, having a fluorescence maximum at 630 nm, were detected with FL2. The ratio of GFP positives in the live cell fraction, and fluorescence intensity were established. As a result, as shown in FIG. 2, by addition of the fusion polypeptide, in both UT-7 and cord blood CD34 positive cells, the ratio of GFP positive cells and fluorescence intensity increased, confirming the improved efficiency of the introduction of adenovirus vector to undifferentiated blood cells.

Example 7

Examination and Quantification of Productivity of CARex-hSCF and CARex-mSCF

Under the same conditions as Example 2, gene introduction into cell lines COS-7 and HEK293T (Pear et al., Proc. Natl. Acad. Sci. USA, Vol. 90, pp. 8392–8396, 1993) was performed with plasmids pcDNA/CARex-hSCF and pcDNA/CARex-mSCF. The obtained culture supernatants were concentrated with Ultrafree, and buffer exchange performed with PBS. Concentrations of the concentrated solutions of CARex-hSCF and CARex-mSCF were respectively measured with a human or mouse SCF quantification ELISA kit (R&D Systems, Minneapolis, U.S.A.). The concentrations of CARex-hSCF produced by COS-7 and HEK293T cell lines were 2.7 μg/ml and 16 μg/ml respectively, and similarly, concentrations of CARex-mSCF were 2.9 μg/ml and 18 μg/ml. That is, a method of measuring concentration of the fusion protein was established and it was confirmed that HEK293T cells were superior to COS-7 cells in respect of productivity of the fusion protein.

Example 8

Cell Surface Antigen Analysis and Infection of Adenovirus for Human Megakaryoblastic Cell Strain M07e For the purpose of cell surface antigen analysis of human megakaryoblastic cell line M07e (available from Dr. Norio Komatu, at Jichi Medical School), approximately $5 \times 10^5$ cells of M07e was apportioned into a 1.5 ml microtube, and subjected to centrifugation at 6000 rmp, for 30 seconds. The supernatant was removed, the cells were washed with PBS and suspended in 50 μl of PBS containing 3% FCS and 0.05% sodium azide (FACS buffer). Phycoerythrin (PE)-labeled anti-human c-Kit antibody (Pharmingen, San Diego, U.S.A.) or PE-labeled anti-human αv-integrin antibody (Cymbus Biotechnology, Chandlers Ford, United Kingdom) or unlabeled anti-human CAR antibody (Upstate Biotechnology, Lake Placid, U.S.A.) was added, and this mixture was allowed to stand for 30 minutes at 4° C. to antibody-label the cells. After washing, the cells labeled with unlabeled anti-human CAR antibody were further secondarily labeled with PE-labeled anti-mouse antibody (Dako, Glostrup, Denmark). After washing, dead cells were stained with 20 μl of 7-aminoactinomycin D (Product name: Via-Probe™, Pharmingen, U.S.A.) for 20 minutes, and after washing the cells, they were suspended in an 0.5 ml FACS buffer. Using a flow cytometer, FACS-LSR (Becton Dickinson), cells were irradiated with 488 nm argon laser light, and PE-labeled cell were detected with FL2 and Via-Probe™-labeled cells detected with FL3. Expression of c-Kit, αv-integrin, CAR in the live cell fraction was observed. As a result of this observation, it was found that M07e strongly expressed both c-Kit and αv-integrin at an expression ratio of 100%, and CAR was hardly expressed at all, at an expression ratio of approximately 1%, similar to that of the negative control. M07e cells ($1 \times 10^5$ cells) were suspended in 0.1 ml of growth medium and apportioned into 48-well plate. CARex-hSCF or CARex-mSCF was added to a final concentration of 10 μng/ml, and further, Ax1CAgfp was added to establish an MOI of 0, 25, 50 or 100. After incubating for 2 hours, cells and medium were collected in a 1.5 ml microtube, subjected to centrifugation at 5000 rpm, for 30 seconds, and the supernatant was removed. Cells were suspended by addition of 0.5 ml of fresh growth medium, inoculated on a new 48-well plate, and further incubated for 16 hours. Results of analysis with FACS-LSR showed that infection with adenovirus alone produced a ratio of GFP positive cells of 0.5% even under conditions of an MOI of 100, which like the negative control was less than 1%. However, in the groups where CARex-hSCF or CARex-mSCF was added, a GFP positive cell ratio of 74% or 82%, respectively, was observed.

Example 9

Influence of Addition of CARex-hSCF and Human SCF Alone of Adenovirus Vector Gene Introduction to UT-7 cells To cell line UT-7, under the same conditions as Example 5, CARex-hSCF was added to a concentration of 10 ng/ml, or human SCF (Peprotech) was added to a concentration of 100 ng/ml. Then Ax1CAgfp was added to establish a MOI of 0, 25, 50 or 100. After incubation, the ratio of GFP positive cells was measured by FACS-LSR. As a result, in the group to which human SCF was added, the GFP positive ratio was similar to that when Ax1CAgfp alone was added (at MOI 100, approximately 20%). However, in the group to which CARex-hSCF was added an improvement in the GFP positive ratio (at MOI 100, approximately 60%) was observed. That is, there is no action of improving efficiency of introduction of adenovirus by addition of human SCF alone, however, it was clear that such an action was obtained by use of a fusion protein of SCF with CAR.

INDUSTRIAL APPLICABILITY

The present invention provides an agent for specific adsorption of type 5 adenoviral vector to undifferentiated blood cells that enables infection with a viral concentration that does not impart toxicity to undifferentiated blood cells, without requiring the construction of a new viral genome or special modification of viral particles such as biotinylation, etc. Use of the polypeptide of the present invention enables improved efficiency of adenoviral vector introduction of any gene to undifferentiated blood cells, and there is provided a method of introducing any gene for which transient expression in these cells is desired. In particular, the method is useful for intracellular DNA recombination by transiently expressing site-specific recombinase, and for induction into any cells of different lines by transient expression of master genes.

All publications, patents and patent applications cited in herein, are incorporated herein in their entirety.

What is claimed is:

1. A linked polypeptide comprising:

(i) a stem cell factor or a single chain anti-CD34 antibody, and (ii) an extracellular region polypeptide of coxsackievirus adenovirus receptor (CAR) protein, wherein said linked polypeptide comprises an amino acid sequence selected from the group consisting of SEQ ID NO: 1, SEQ ID NO:2 and SEQ ID NO:3.

2. The linked polypeptide according to claim 1, which comprises the amino acid sequence of SEQ ID NO: 1.

3. The linked polypeptide according to claim 1, which comprises the amino acid sequence of SEQ ID NO: 2.

4. The linked polypeptide according to claim 1, which comprises the amino acid sequence of SEQ ID NO: 3.

* * * * *